US012605253B2

(12) United States Patent
Dusterhoft et al.

(10) Patent No.: US 12,605,253 B2
(45) Date of Patent: Apr. 21, 2026

(54) EXPANDABLE CORPECTOMY MODULAR ENDPLATE CONNECTION

(71) Applicant: Astura Medical Inc., Iriving, TX (US)

(72) Inventors: Ross Dusterhoft, Irving, TX (US); Thomas Purcell, Irving, TX (US)

(73) Assignee: ASTURA MEDICAL INC, Irving, TX (US)

( * ) Notice: Subject to any disclaimer, the term of this patent is extended or adjusted under 35 U.S.C. 154(b) by 0 days.

(21) Appl. No.: 18/920,849

(22) Filed: Oct. 18, 2024

(65) Prior Publication Data

US 2025/0127628 A1 Apr. 24, 2025

Related U.S. Application Data

(60) Provisional application No. 63/544,783, filed on Oct. 18, 2023.

(51) Int. Cl.
*A61F 2/44* (2006.01)
*A61F 2/30* (2006.01)

(52) U.S. Cl.
CPC ............ *A61F 2/4465* (2013.01); *A61F 2/442* (2013.01); *A61F 2002/30092* (2013.01); *A61F 2002/30113* (2013.01); *A61F 2002/30153* (2013.01); *A61F 2002/30405* (2013.01); *A61F 2002/30523* (2013.01); *A61F 2002/30553* (2013.01); *A61F 2002/30579* (2013.01)

(58) Field of Classification Search
CPC .. A61F 2002/30601; A61F 2002/30405; A61F 2/4455; A61F 2/44; A61F 2/446
See application file for complete search history.

(56) References Cited

U.S. PATENT DOCUMENTS

| | | | | |
|---|---|---|---|---|
| 8,591,587 B2 * | 11/2013 | Refai | .................... | A61F 2/4637 |
| | | | | 623/17.15 |
| 9,301,850 B2 * | 4/2016 | Mclaughlin | ............. | A61F 2/446 |
| 10,376,373 B2 * | 8/2019 | Howard | ................ | A61F 2/4455 |
| 10,758,365 B2 * | 9/2020 | Cummins | ........... | A61F 2/30771 |
| 10,881,521 B2 * | 1/2021 | Howard | .................. | A61F 2/442 |
| 12,496,196 B2 * | 12/2025 | Smith | ..................... | A61F 2/442 |
| 2010/0179655 A1 * | 7/2010 | Hansell | .................. | A61F 2/442 |
| | | | | 623/17.11 |
| 2010/0324687 A1 * | 12/2010 | Melkent | .................... | A61F 2/44 |
| | | | | 623/17.16 |
| 2012/0130493 A1 * | 5/2012 | McLaughlin | ............. | A61F 2/44 |
| | | | | 623/17.16 |
| 2012/0197398 A1 * | 8/2012 | Miller | ...................... | A61F 2/44 |
| | | | | 623/17.11 |
| 2013/0331943 A1 * | 12/2013 | Arnold | .................. | A61F 2/4611 |
| | | | | 623/17.15 |
| 2014/0156006 A1 * | 6/2014 | Bannigan | .................. | A61F 2/44 |
| | | | | 623/17.15 |

(Continued)

FOREIGN PATENT DOCUMENTS

WO WO-2021174247 A1 * 9/2021 ........... A61F 2/4455

OTHER PUBLICATIONS

International Search Report and Written Opinion in PCT Application No. PCT/US2024/052145 dated Jan. 8, 2025.

*Primary Examiner* — Jacqueline T Johanas
(74) *Attorney, Agent, or Firm* — Michael R Shevlin

(57) ABSTRACT

A vertebral body replacement system having a quick-connecting removable endplate connection mechanism.

9 Claims, 7 Drawing Sheets

(56)     References Cited

U.S. PATENT DOCUMENTS

| 2015/0032210 A1* | 1/2015 | Stinchfield | ............... A61F 2/44 |
| | | | 623/17.16 |
| 2016/0278933 A1* | 9/2016 | Semler | .................. A61F 2/4611 |
| 2018/0318107 A1* | 11/2018 | Cummins | ........... A61F 2/30771 |
| 2022/0401227 A1* | 12/2022 | Semler | .................. A61F 2/4455 |
| 2023/0115853 A1* | 4/2023 | Harper | .................. A61F 2/4465 |
| | | | 606/246 |
| 2025/0127628 A1* | 4/2025 | Dusterhoft | .............. A61F 2/442 |

* cited by examiner

165a

165b

165c

165d

EXPANDABLE CORPECTOMY MODULAR ENDPLATE CONNECTION

CROSS-REFERENCE TO RELATED APPLICATIONS

This application claims the benefit of U.S. Provisional Application No. 63/544,783, titled EXPANDABLE CORPECTOMY MODULAR ENDPLATE CONNECTION, filed Oct. 18, 2023, which is incorporated herein by reference.

This application is related to U.S. Provisional Application No. 63/544,784, titled AUTO-LOCKING EXPANDABLE CORPECTOMY COLUMN, filed Oct. 18, 2023, which is incorporated herein by reference.

FIELD

The present invention relates generally to the field of surgery, and more specifically, to a vertebral body replacement device (i.e., "VBR") for placement in spinal fusion surgery.

BACKGROUND

A corpectomy or vertebrectomy is a surgical procedure that involves removing all or part of the vertebral body, usually as a way to decompress the spinal cord and nerves. When the vertebral body has been removed, the surgeon performs a vertebral fusion. Because a space in the column remains from the surgery, the surgeon may insert a vertebral body replacement (VBR) system to fill the space.

Current vertebral body replacement systems typically consist of an expanding column-like central member with two endplates on either end. Current systems utilize a variety of methods of securing the endplates to the expanding columns including screws, collets, and press-fits. These methods are often time consuming, take additional instrumentation to facilitate, and may not be able to be disassembled.

Some prior art system include:

a vise to compress the endplates onto the column where flexible members on the column flex open before dropping onto a ledge on the endplates;

screw components that thread the endplates onto the column;

a garter spring in addition to two lateral set screws;

a tapered press fit between the column and endplates;

living springs on each endplate that latch into grooves on the columns;

a snap ring in the endplate that expands then collapses into a groove on the column when assembled.

The prior art systems do not solve the aforementioned problems for the reasons discussed below;

a vise to compress the endplates onto the column where flexible members on the column flex open before dropping onto a ledge on the endplates;

screw components that thread the endplates onto the column;

a garter spring in addition to two lateral set screws;

a tapered press fit between the column and endplates;

living springs on each endplate that latch into grooves on the columns;

a snap ring in the endplate that expands then collapses into a groove on the column when assembled.

It would be desirable to develop a vertebral body replacement system having a quick-connecting removable endplate connection mechanism.

SUMMARY

Disclosed is a vertebral body replacement system having a quick-connecting removable endplate connection mechanism.

DETAILED DESCRIPTION

The vertebral body replacement system disclosed includes a central member or expandable column with modular endplate connections at each end having a quick connect mechanism for changing endplates after assembly.

Some of the features of the disclosed vertebral body replacement system include:

Modular endplate connections are the same on both sides of the central member.

Quick connect mechanism includes endplate mating rings housed within the central member and not the endplates.

Disassembly instrument engages the endplate mating rings externally to remove the endplate and does not require access to the full ID of the implant.

Assembly process does not require substantial force to perform.

Assembly process does not require additional instrumentation, such as a vise or mallet, to perform.

Central member and endplates include a mating spline feature that accomplishes multiple tasks simultaneously:

It maximizes contact area between the endplate ring and endplate;

It indexes the endplate to the spline at a high resolution of 15° before the endplate ring begins to compress;

It is the torque bearing feature between the endplates and the column;

It allows for the endplate to be removed from the column even when the disassembly pins are fully compressed; and It allows the endplate ring to remain engaged in the groove in the column, removing the need for centering the ring prior to assembly.

The improvements made by the vertebral body replacement system disclosed include:

Reduced inventory through the modularity of the endplates;

Reduced component count by keeping the endplate rings in the column instead of the endplates, which have far more SKUs;

External disassembly instrument allowing full use of the ID of the implant for mechanism design;

Material efficient Quick-connect mechanism that is low profile while being high strength and may be used on cervical implants;

Low force assembly process which reduces the chance of damaged implants or injury; and High resolution of endplate orientations is achieved through the spline.

Figure 1:
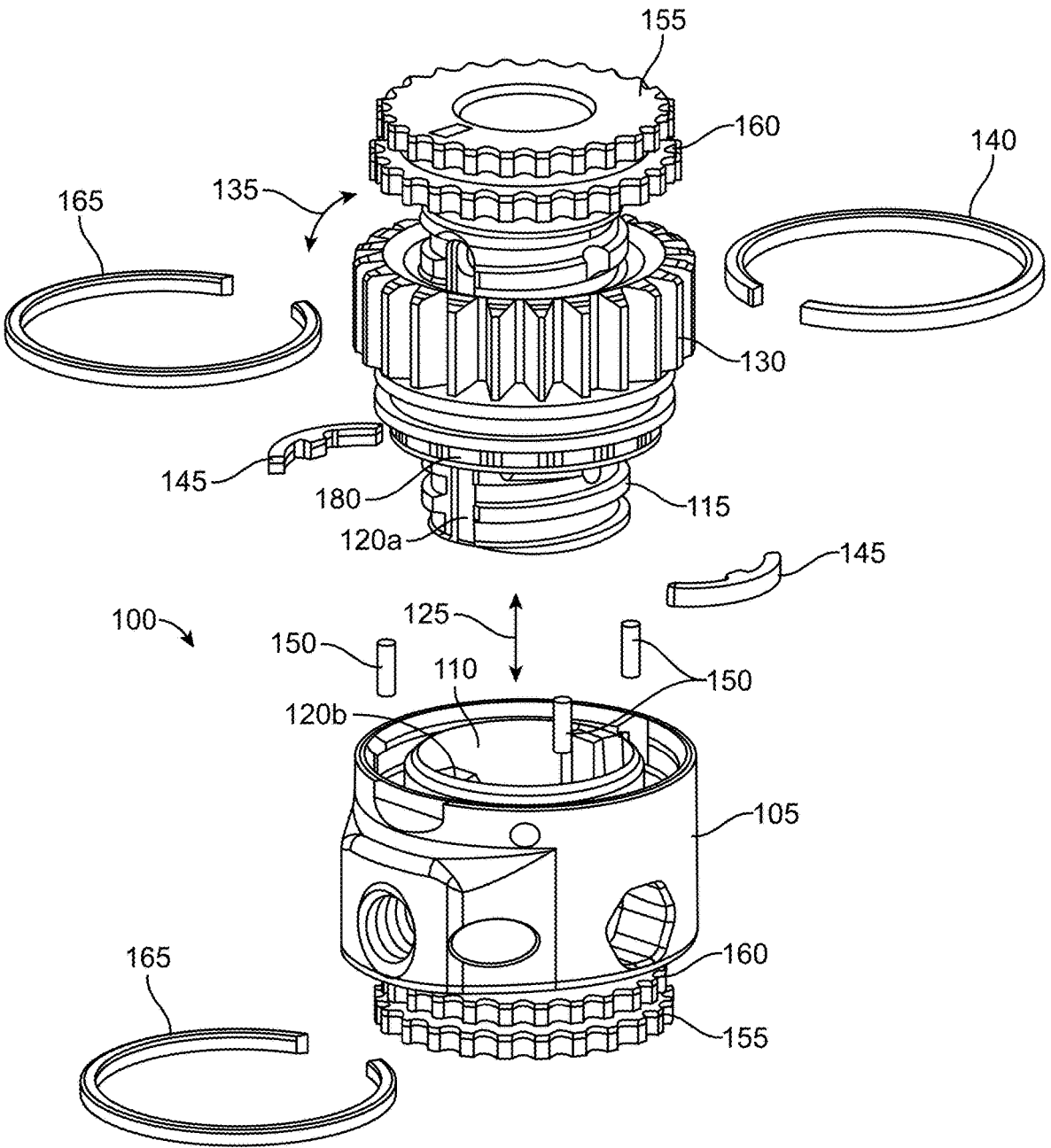
FIG. 1 is an exploded perspective view showing one embodiment of an expandable column.

FIG. 1 is an exploded perspective view showing one embodiment of an expandable column 100 having a body 105 with a central opening 110, a threaded column 115 is configured to sliding fit within the central opening 110. The opening 110 and threaded column 115 include axial translation mating features 120a, 120b to allow the threaded column to translate column up and down 125. Axial translation of the threaded column 115 done with a drive gear 130. The drive gear 130 includes internal threads rotatingly coupled to the threaded column and a lower portion rotatingly coupled with the body with a retaining ring 140. Multiple up-stop tabs 145 are configured to prevent over expansion of the threaded column 115. Multiple springs 150 include a lower portion pressed into spring holes in the body 105 and an upper portion engaging a drive gear track 180 on the drive gear 130 to regulate directional rotation of the drive gear 130, allowing rotation in a first direction and preventing rotation in a second direction. In use, the drive gear 130 is rotated 135 to translate the threaded column 115 up or down. The body 105 contains features for instrumentation to be attached and operated as well as graft windows for bone growth.

Both ends of the expandable column 100 include endplate mating splines 155 with a groove or slot 160. An endplate ring 165 is configured to be inserted in the groove or slot 160. The endplate ring 165 is made of a flexible material that can be radially compressed with a radial compression force, and then expand back to the original shape once the radial force is removed. The endplate ring 165 may be comprised of different materials, such as titanium or nitinol (NiTi).

Figure 2:
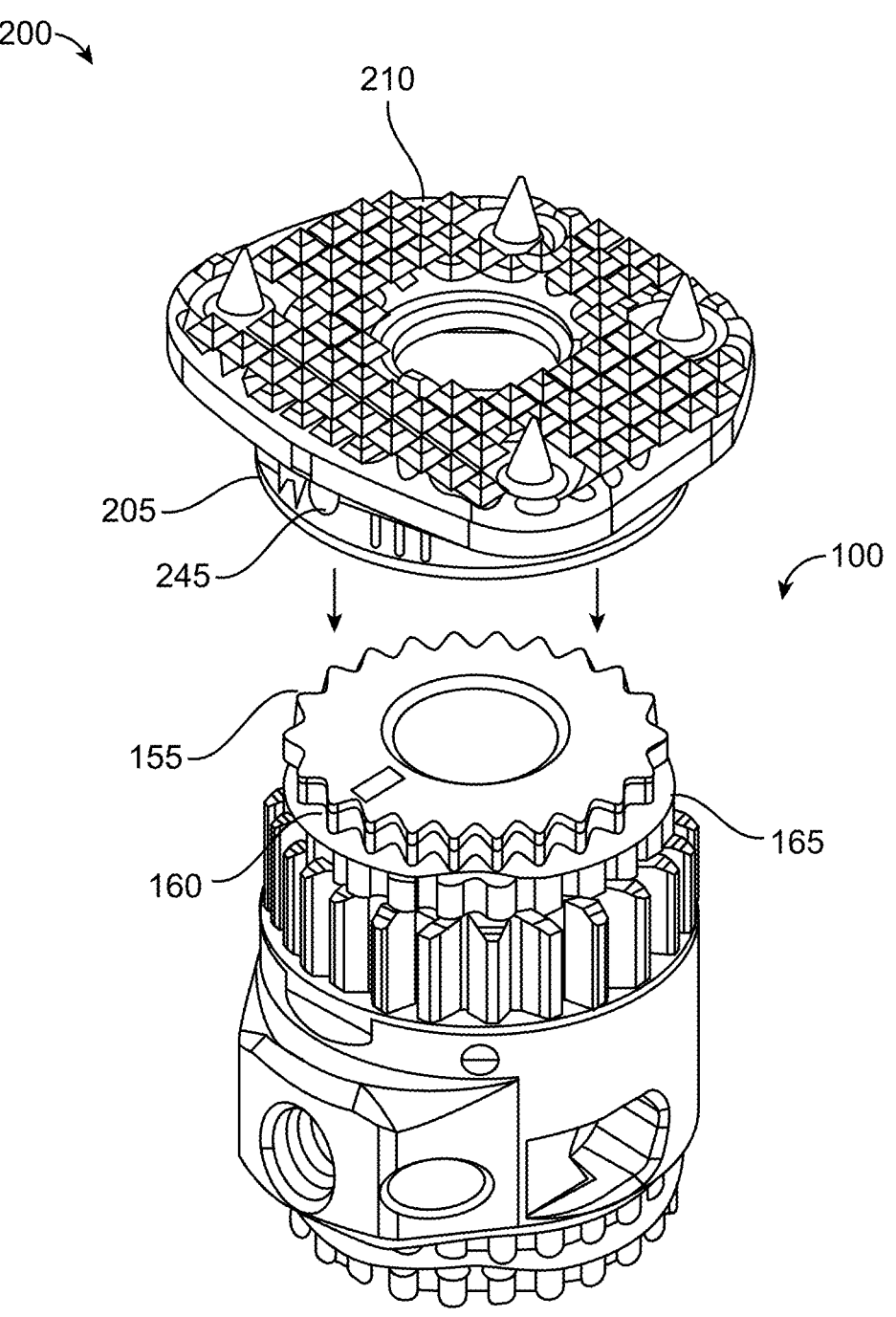
FIG. 2 is an exploded perspective view showing an endplate approaching the expandable column.

FIG. 2 is an exploded perspective view showing an endplate 200 approaching the expandable column 100. The endplate 200 includes a lower cylindrical wall 205 with an internal column mating spline with endplate groove surrounding a central opening sized to receive the endplate mating spline 155. The endplate 200 also includes an upper surface 210 configured to contact a vertebra. The upper surface 210 may vary in shape and/or geometry for the different spinal locations and/or anatomical needs.

The internal column mating spline is configured to couple with the endplate mating spline 155.

Assembly

Figure 3A:
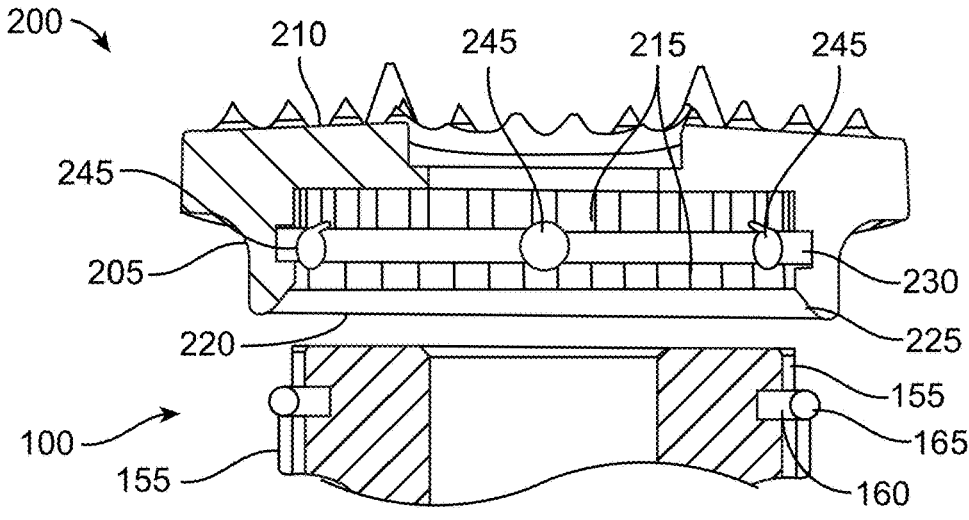
FIGS. 3A-3C are cross-sectional side views showing the endplate being assembled with the expandable column.
Figure 3B:
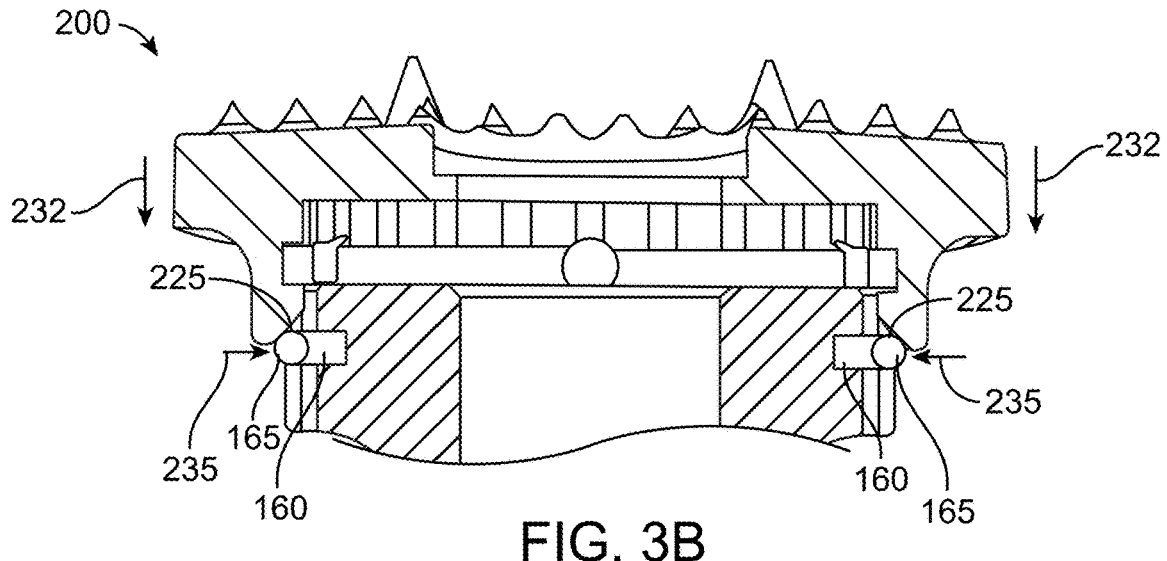
Figure 3C:
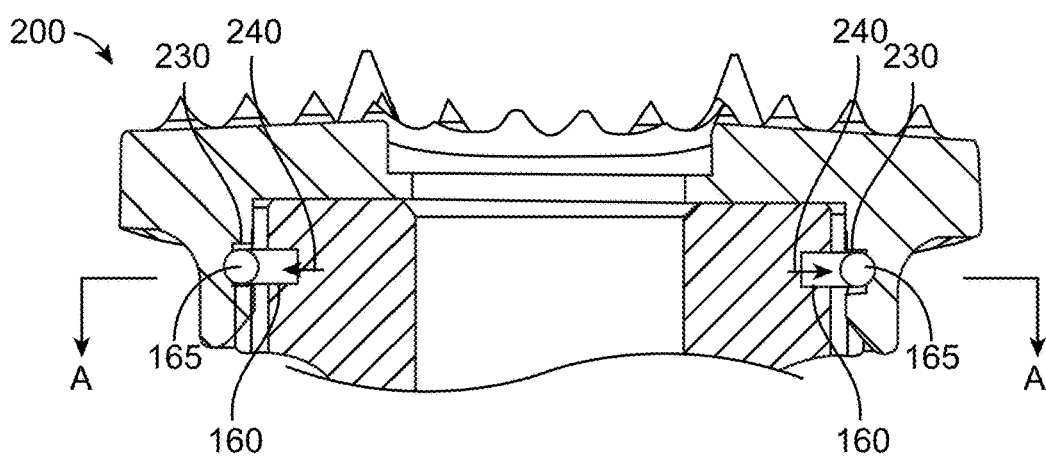

FIGS. 3A-3C are cross-sectional side views showing the endplate 200 being assembled with the expandable column 100. FIG. 3A is a cross-sectional view showing the endplate 200 positioned above the expandable column 100. The endplate 200 includes the lower cylindrical wall 205 with an internal column mating spline 215 surrounding a central opening 220 sized to receive the endplate mating spline 155. A lower portion of the wall 205 includes an internal countersink creating a tapered portion 225 configured to engage the endplate ring 165. The wall also includes an endplate groove 230 in the wall 205 that is sized to receive the endplate ring 165.

The endplate mating spline 155 and column mating spline 215 include mating spline features that allow placement of the endplate 200 at different orientations. In the embodiment shown, the mating spline features of the endplate mating spline 155 and column mating spline 215 include a plurality of teeth configured to allow the endplate 200 to be joined with the expandable column 100 in different orientations. For example, the endplate 200 may be positioned at any 15-degree orientation on the expandable column 100.

FIG. 3B is a cross-sectional view showing the endplate 200 first indexed to the expandable column 100. As the endplate 200 is lowered on the expandable column 100, the endplate mating spline 155 and column mating spline 215 are partially engaged and the tapered portion 225 contacts the endplate ring 165. As a downward force 232 is applied to the endplate 200, the tapered portion 225 applies an inward radial force 235 to the endplate ring 165 which radially compresses the endplate ring 165 into the column groove 160.

FIG. 3C is a cross-sectional view showing the endplate 200 assembled to the expandable column 100 with the endplate mating spline 155 engaged with the column mating spline 215. In this position, the end plate groove 230 is positioned next to the column groove 160 and the compressed endplate ring 165 radially expands 240 into the endplate groove 230, locking the endplate 200 to the expandable column 100.

Figure 4A:
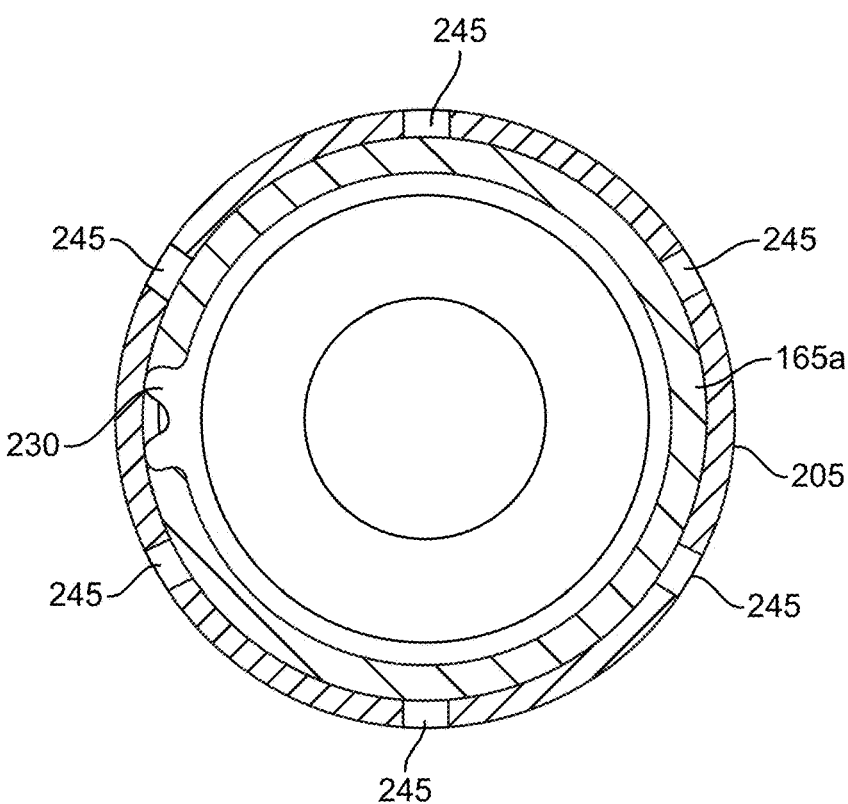
FIGS. 4A and 4B are top sectional views showing the endplate assembled on the expandable column.

FIG. 4A is top sectional view at A-A showing the endplate 200 assembled on the expandable column 100 with a circular endplate ring 165a with a pre-formed circular cross section. The circular endplate ring 165a is radially expanded into the endplate groove 230 locking the endplate 200 with the expandable column 100.

Figure 4B:
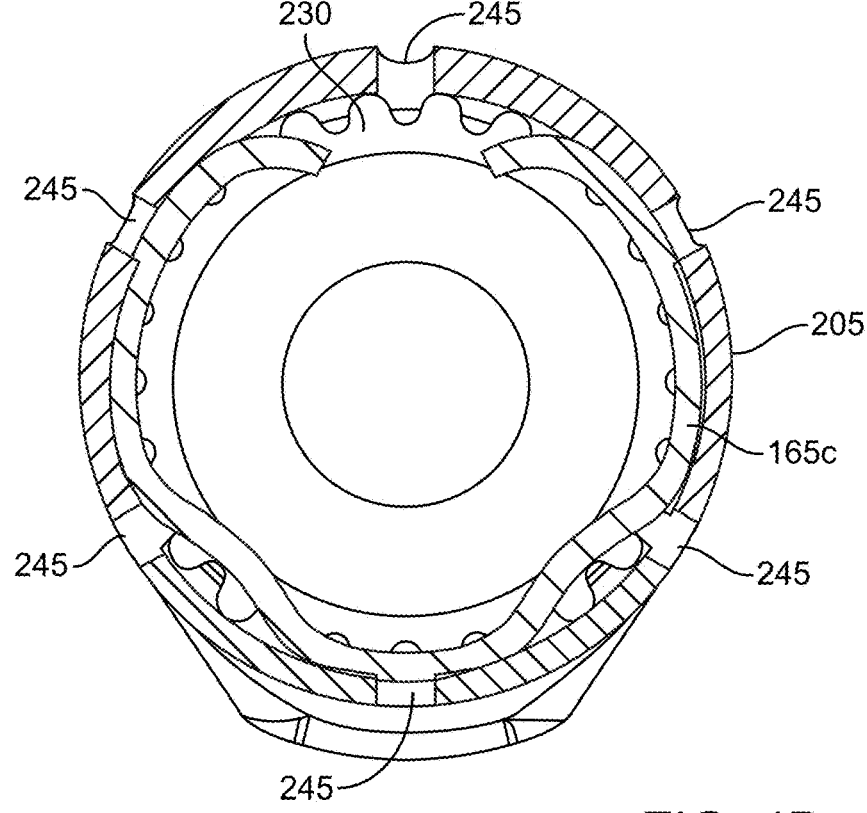
Figure 5A:
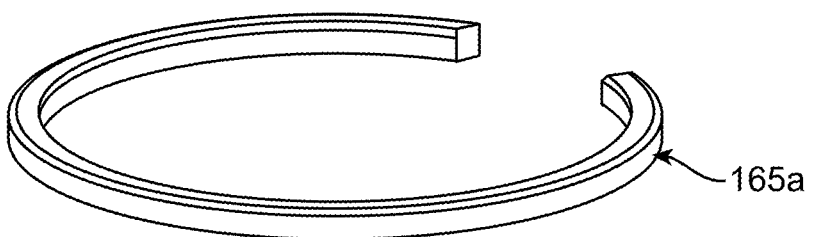
FIGS. 5A-5D are perspective views showing different types of endplate rings.
Figure 5B:
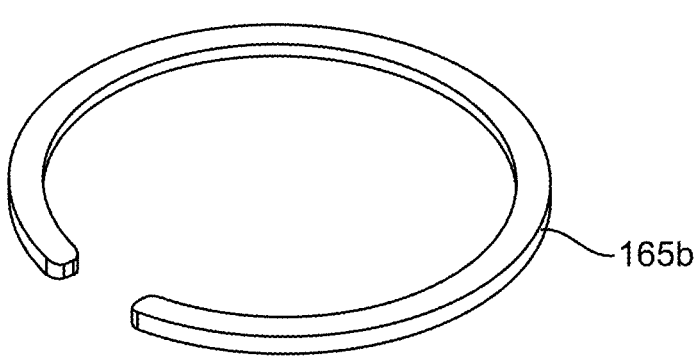
Figure 5C:
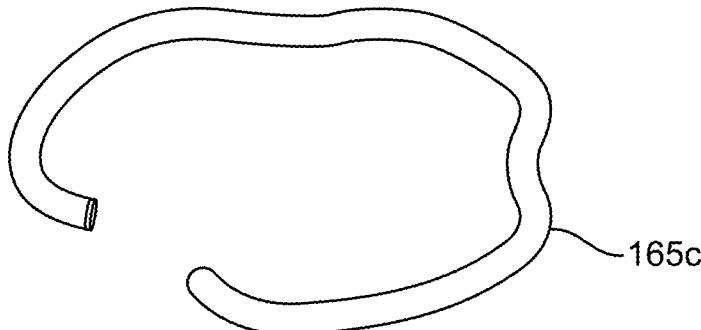
Figure 5D:
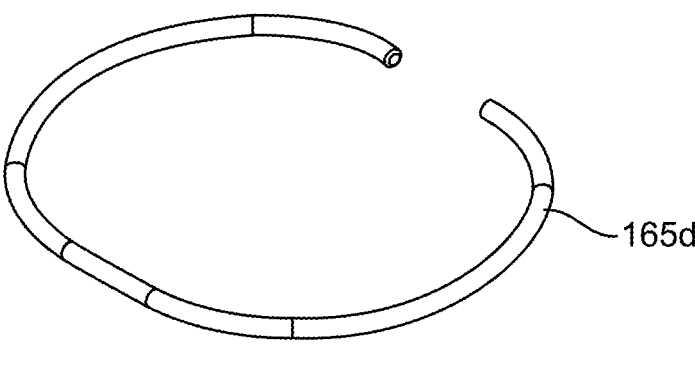

FIG. 4B is top sectional view at A-A showing the endplate 200 assembled on the expandable column 100 with a pre-formed endplate ring 165c with a circular cross section.

FIGS. 5A-5D are perspective views showing different types of endplate rings 165. The endplate rings are designed to maintain interference with at least one of its connected members to reduce toggle in the assembly. The figures show some example endplate rings, including: a circular endplate ring 165a having a round cross section, a circular endplate ring 165b having a rectangular cross section; a pre-formed endplate ring 165c having a circular cross section; and an alternate pre-formed endplate ring 165d having a circular cross section.

Referring back to FIGS. 4A, 4B, the endplate 200 also includes multiple external holes 245 extending through the wall 205 to access the endplate ring 165 in the endplate groove 230. The external holes 245 may be used with a disassembly instrument designed to unlock the endplate 200 from the extended column 100 for removal.

Disassembly

A disassembly instrument 300 may be used to remove the endplate 200 from the expanded column 100. The disassembly instrument 300 is configured to couple with the endplate and utilize the external holes 245 contact the endplate ring 165 and apply force to collapse the endplate ring 165 into the column groove 160 to unlock the endplate 200 from the expanded column 100, allowing the removal of the endplate 200 with a small amount of force 320. The disassembly instrument 300 may be used to remove and replace the endplate 200 with a different endplate shape or endplate configuration. The disassembly instrument 300 may also be used to remove the endplate 200 to change the orientation or direction on the expandable column 100. The disassembly instrument 300 may be used with any endplate on either end of the expandable column 100.

Figure 6A:
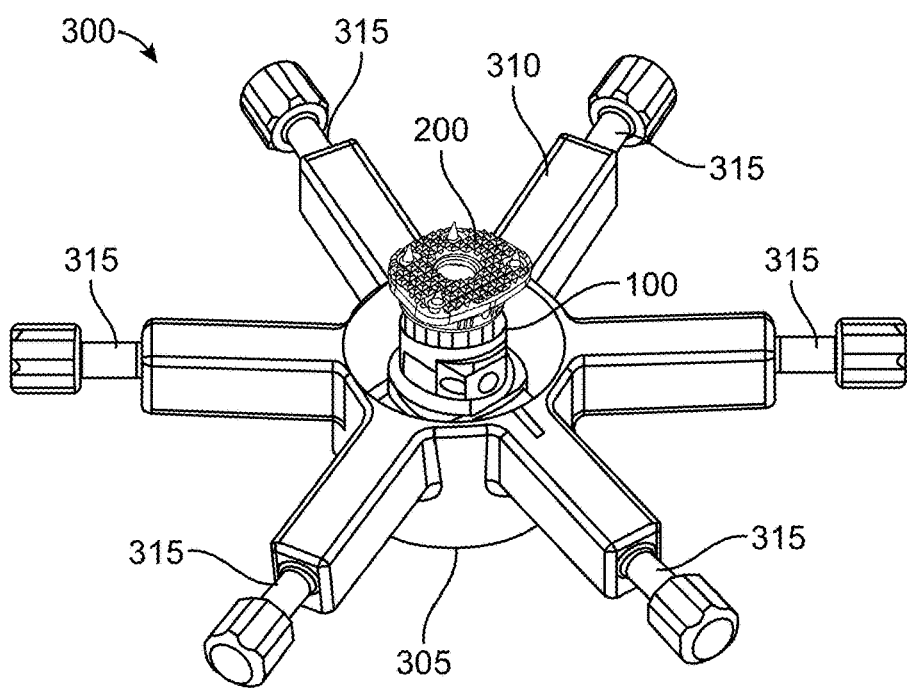
FIGS. 6A, 6B show a disassembly instrument coupled with an endplate
Figure 6B:
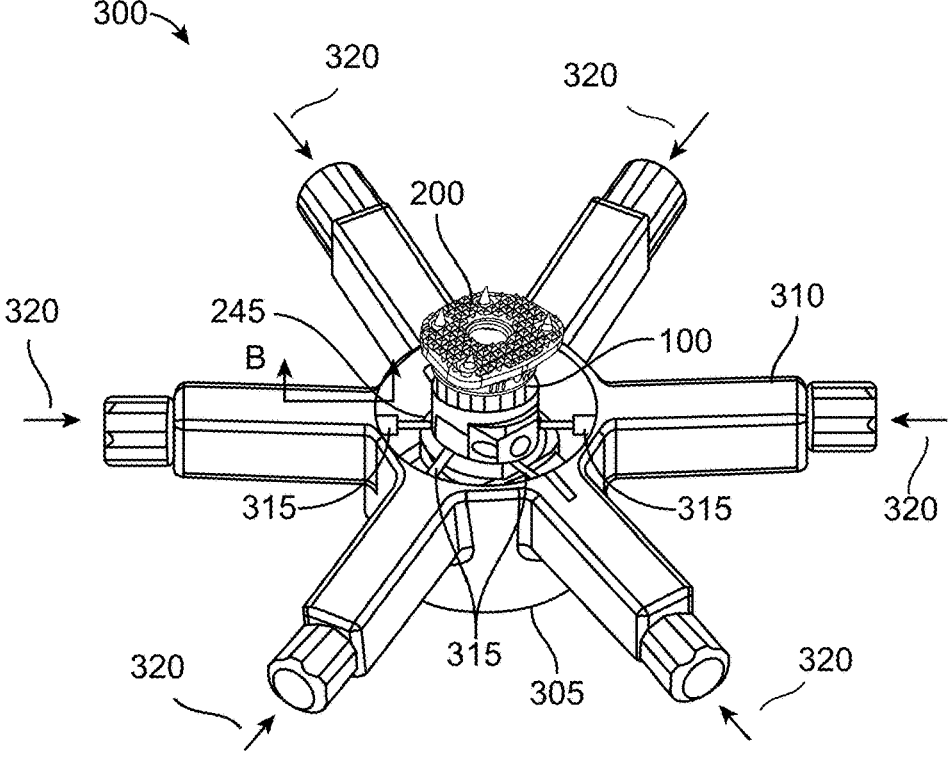
Figure 6C:
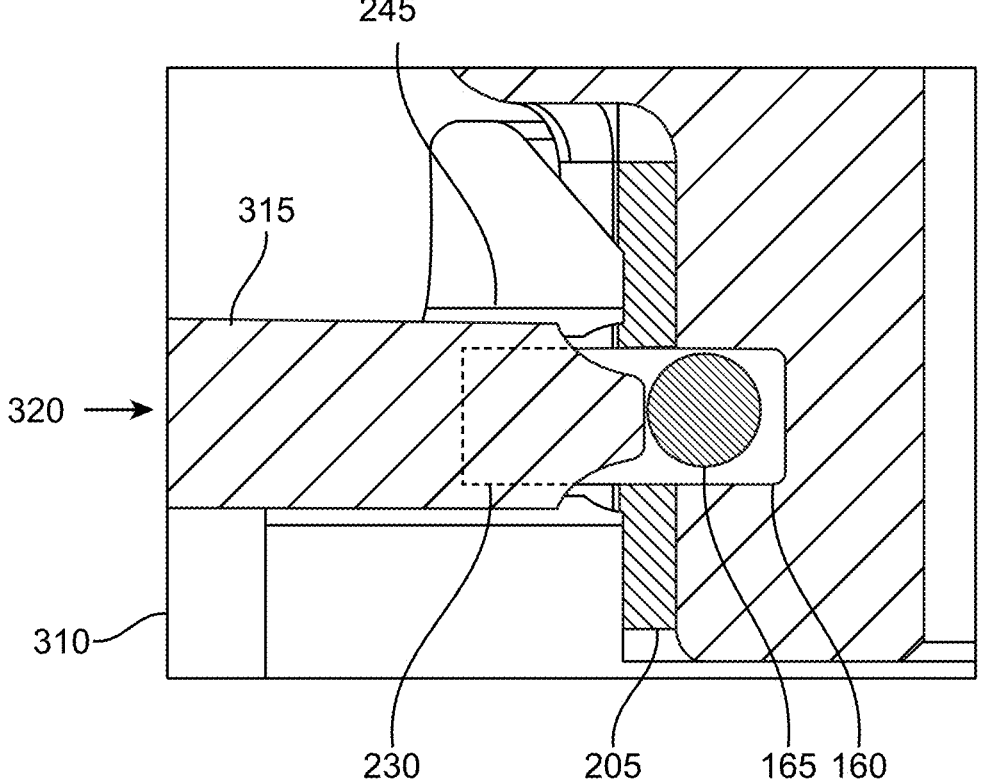
FIG. 6C is a cross-sectional view showing engagement of a disassembly pin with the endplate ring.

FIGS. 6A, 6B show a disassembly instrument 300 coupled with an endplate 200 and FIG. 6C is a cross-sectional view showing engagement of a disassembly pin 315 with the endplate ring 165. The disassembly instrument 300 includes a body 305 configured to couple with the endplate 200 and multiple arms 310 extending radially from the body 305 positioned proximate the external holes 245. Each of the arms 310 includes a disassembly pin 315 designed to extend through the external hole 245 to engage the endplate ring 165. FIG. 6A shows attachment of the disassembly instrument 300 coupled with an endplate 200 with the disassembly pins 315 in a retracted position. FIG. 6B shows disassembly instrument 300 in the endplate ring engagement position with the disassembly pins 315 translated inwardly through the external holes 245 to engage the endplate rings 165. FIG. 6C shows the disassembly pin 315 320 applying a radial force 320 to the endplate ring 165 and compress or collapse the endplate ring 165 into the column groove 160. Once all the disassembly pins 320 are in the ring compressed position, the endplate 200 is unlocked and may be removed from the expanded column 100.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. An expandable column with modular endplate connections comprising:
   a body having body endplate mating splines with a body endplate mating groove;
   a body endplate ring with an original shape positioned in the body endplate mating groove;
   a body endplate having body mating splines with a body mating groove, the body mating splines configured to couple with the body endplate mating splines and radially compress the body endplate ring into the body endplate mating groove with a radial compression force and then radially expand back to the original shape in the body mating groove to lock the body endplate to the body;
   a threaded column axially coupled to the body, the threaded column having column endplate mating splines with a column endplate mating groove;
   a column endplate ring with an original shape positioned in the column endplate mating groove;
   a column endplate having threaded column mating splines with a threaded column mating groove, the threaded column mating splines configured to couple with the column endplate mating splines and radially compress the column endplate ring into the column endplate mating groove with a radial compression force and then radially expand back to the original shape in the threaded column mating groove to lock the column endplate to the column; and
   a drive gear threaded onto the threaded column and coupled to the body, the drive gear being configured to rotate and translate the threaded column axially up or down.

2. The expandable column of claim 1, wherein the endplate rings are comprised of super-elastic material or nitinol.

3. The expandable column of claim 1, wherein the body endplate includes an upper surface configured to contact a vertebra, the upper surface may vary in shape and/or geometry for the different spinal locations and/or anatomical needs.

4. The expandable column of claim 1, wherein the endplate mating spline and column mating spine include a plurality of teeth configured to allow the endplate to be joined with the expandable column in different orientations.

5. The expandable column of claim 1, wherein the body and column endplate rings are circular endplate rings having a round cross section.

6. The expandable column of claim 1, wherein the body and column endplate rings are circular endplate rings having a rectangular cross section.

7. The expandable column of claim 1, wherein the endplates include multiple external holes extending through a wall of each endplate to access the body and column endplate rings in the body and threaded column endplate mating grooves.

8. The expandable column of claim 1, further comprising a disassembly instrument designed to unlock the body and column endplates for removal.

9. An expandable column with modular endplate connections comprising:
   a body having central opening;
   a threaded column with a drive gear configured to slidingly fit into the central opening of the body and to rotate and translate the threaded column axially up or down, the threaded column having endplate mating splines with a column groove;
   an endplate ring with an original shape configured to be inserted in the column groove;
   an endplate having column mating splines with an endplate groove configured to couple with the endplate mating splines, the endplate mating splines configured to radially compress the endplate ring into the column groove with a radial compression force, and then expand radially back to the original shape in the endplate groove and the radial force is removed to lock the endplate to the threaded column.

* * * * *